United States Patent [19]
Shimonishi et al.

[11] Patent Number: 6,013,502
[45] Date of Patent: Jan. 11, 2000

[54] GENE OF CELL WALL LYTIC ENZYME, AND VECTOR CONTAINING SAID GENE AND TRANSFORMANT

[75] Inventors: Tsuyoshi Shimonishi; Satoshi Kaneko; Satoru Nirasawa, all of Tsukuba; Kiyoshi Hayashi, Tsuchiura; Kazutomo Haraguchi, Tsukuba, all of Japan

[73] Assignees: Director of National Food Research Institute, Ministry of Agriculture, Forestry and Fisheries, Tsukuba; Bio-oriented Technology Research Advanced Institution, Omiya, both of Japan

[21] Appl. No.: 09/040,285

[22] Filed: Mar. 18, 1998

[30] Foreign Application Priority Data

Dec. 1, 1997 [JP] Japan .................................. 9-343630

[51] Int. Cl.[7] ............................. C12N 9/36; C12N 15/56; C12N 15/63
[52] U.S. Cl. ................... 435/206; 435/320.1; 435/252.3; 435/252.33; 435/200; 536/23.2
[58] Field of Search ........................ 536/23.2; 435/252.3, 435/252.33, 230.1, 206, 200

[56] References Cited

U.S. PATENT DOCUMENTS

| | | | |
|---|---|---|---|
| 5,326,858 | 7/1994 | Lichenstein et al. | 536/23.2 |
| 5,336,609 | 8/1994 | Oberto et al. | 435/206 |

FOREIGN PATENT DOCUMENTS

| | | |
|---|---|---|
| 0 297 598 | 1/1989 | European Pat. Off. . |
| 0 368 224 | 5/1990 | European Pat. Off. . |
| 37 04 004 | 8/1988 | Germany . |
| WO 91/06009 | 4/1991 | WIPO . |
| WO 91/06009 | 5/1991 | WIPO . |

OTHER PUBLICATIONS

Croux C, et al. Sequence of the lyc gene encoding the autolytic lysozyme of *Clostridium acetobutylicum* ATCC824: comparison with other lytic enzymes. Gene, 1991, vol. 104(1), pp. 25–31, Aug. 1991.

Bush JW. Enzymatic lysis of the pseudomurein–containing methanogen *Methanobacterium formicicum*. J Bacteriol, 1985, vol. 163(1), pp. 27–36, Aug. 1985.

Garcia E, et al. Molecular evolution of lytic enzymes of *Streptococcus pneumoniae* and its bacteriophages. Proc Natl Acad Sci U S A, 1988, vol. 85(3), pp. 914–918, Feb. 1988.

Kiyoshi Hayashi, et al., Agricultural and Biological Chemistry, vol. 48, No. 2, pp. 465–471, "Properties of N–Acetylmuramidase from *Streptomyces Rutgersensis* H–46[+]", 1984.

Hayashi, et al., "Effects of N–Acetylmuramidase from *Streptomyces rutgersensis* H–46 as a Food Preservative", Agric. Biol. Chem., 53 (12), (1989), pp. 3173–3171.

Hayashi, et al. "Purification and Characterization of the Lytic Enzyme Produced by *Streptomyces rutgersensis* H–46", Agric. Biol. Chem., 45 (10), (1981), pp. 2289–2300.

Hayashi, et al., "Bacteriolytic Enzyme Produced by Streptomyces sp.", J. Ferment Technol., vol. 59, No. 4, (1981), pp. 319–323.

*Primary Examiner*—Ponnathapu Achutamurthy
*Assistant Examiner*—Bradley S. Mayhew
*Attorney, Agent, or Firm*—Oblon, Spivak, McClelland, Maier & Neustadt, P.C.

[57] ABSTRACT

The present invention relates to polynucleotides encoding particular N-acetylmuramidases, which are cell wall lytic enzymes, of *Streptomyces rutgersensis* origin. The invention also relates to vectors comprising the polynucleotides encoding the N-acetylmuramidases, and also relates to host cells transformed with the vectors.

19 Claims, No Drawings

GENE OF CELL WALL LYTIC ENZYME, AND VECTOR CONTAINING SAID GENE AND TRANSFORMANT

FIELD OF THE INVENTION

The present invention relates to a gene of a cell wall lytic enzyme, and a plasmid vector containing said gene and a transformant.

BACKGROUND OF THE INVENTION

A cell wall lytic enzyme is an enzyme degrading the cell wall of bacteria including Actinomycetes, and on the action of the enzyme, the bacterial cell wall is decomposed, leading to the death of the bacteria.

The outer layer of bacteria is covered with cell wall, and the principal structural component of the cell wall is a peptide glycan comprising sugar chains and peptides. The cell wall lytic enzyme acts on the peptide glycan.

When the enzyme acts on the peptide glycan, the enzyme reacts with the sugar chain of the peptide glycan to generate N-acetylmuramic acid from the sugar at the terminus to be reduced. Therefore, the enzyme is classified as N-acetylmuramidase.

Major enzymes to be classified as N-acetylmuramidase include lysozyme derived from chicken egg white. However, the cell wall lytic enzyme is different from these enzymes in terms of enzymatic and chemical properties and the subjective microorganisms to be decomposed [Hayashi K., et al., Agric. Biol. Chem. (European Edition of Japanese Journal of Agriculture, Biochemistry and Chemistry), Vol. 45, pp. 2289–2300, 1981], and the enzyme has novel specificities.

As has been described above, the cell wall lytic enzyme decomposes bacterial cell wall, and by utilizing the property, the enzyme is used for extracting enzymes and DNA present in the inside of bacteria.

Because some bacteria may be killed through the action of the present enzyme, furthermore, the enzyme may be utilized as food preservative [Hayashi K., et al., Agric. Biol. Chem. (European Edition of Japanese Journal of Agriculture, Biochemistry and Chemistry), Vol. 53, pp. 3173–3177, 1989].

Conventional methods for recovering the cell wall lytic enzyme include a method comprising culturing microorganisms, such as Actinomycetes belonging to genus Streptomyces, and bacteria belonging to genera Achromobacter, Aeromonas, Bacillus, Clostridium, Flavobacterium, Myxobacter, Myxococcus, Pseudomonas, Staphylococcus and Streptococcus, and preparing the objective enzyme from the culture filtrate or the cultured bacteria. When the cell wall lytic enzyme is egg white-derived lysozyme, use is made of a method comprising preparing the enzyme by utilizing isoelectric precipitation and the like.

The enzyme recovered by these methods is commercially available as crude enzyme or purified enzyme. However, these methods are not satisfactory as methods for producing the enzyme in a stable fashion.

For further promotion of the utilization of cell wall lytic enzymes, an object of the present invention resides in making contribution to the industrial production of cell wall lytic enzymes, by cloning the gene of said enzymes to elucidate the structure of the gene and expressing said gene.

SUMMARY OF THE INVENTION

The present inventors have made investigations so as to overcome the problems described above. Then, the inventors have designed the cloning of the gene of a cell wall lytic enzyme from the microorganisum belonging to genus Streptomyces. The inventors have successfully cloned the gene. Thus, the present invention has been achieved.

The invention according to claim 1 is the gene of a precursor of a cell wall lytic enzyme derived from genus Streptomyces, the gene having the nucleotide sequence as Sequence No. 1 in the Sequence Listing.

The invention according to claim 2 is a plasmid containing the gene of the precursor of the cell wall lytic enzyme, according to claim 1.

The invention according to claim 3 is an *E. coli* (FERM BP-6166) transformed with the plasmid according to claim 2.

The invention according to claim 4 is the gene of a cell wall lytic enzyme derived from genus Streptomyces, the gene having the nucleotide sequence as Sequence No. 2 in the Sequence Listing.

The invention according to claim 5 is a plasmid containing the gene of the cell wall lytic enzyme, according to claim 4.

The invention according to claim 6 is an *E. coli* transformed with the plasmid according to claim 5.

DETAILED DESCRIPTION OF THE INVENTION

The present inventors extracted a cell wall lytic enzyme, from a bacterium, which has an ability of producing a cell wall lytic enzyme, belonging to the genus Streptomyces, to purify the enzyme at high purity and determine the amino acid sequence of the N-terminus (see Sequence No. 3 in the Sequence Listing). Furthermore, on the basis of the amino acid sequence determined, a pair of primers were prepared (see Sequence Nos. 4 and 5 in the Sequence Listing). By polymerase chain reaction (PCR) with the genomic DNA extracted from a bacterium belonging to the genus Streptomyces as a template by using the primers mentioned above, a prominent band of 140 bp was recovered.

By cloning the resulting band (PCR product) and analyzing the band with a DNA sequencer, the DNA nucleotide sequence thereof was determined (see Sequence No. 6 in the Sequence Listing). The DNA nucleotide sequence was then translated into amino acid. It was observed a sequence corresponding to the preliminarily recovered amino acid sequence at the N-terminus (see Sequence No. 3 in the Sequence Listing), which indicates that said PCR product was a part of the gene of the cell wall lytic enzyme.

Then, the gene of the cell wall lytic enzyme was firstly cloned by using the PCR product as the probe.

Alternatively, the genomic DNA extracted from the bacterium belonging to the genus Streptomyces was enzymatically degraded, to subject the resulting DNA fragments to Southern hybridization. Consequently, it was confirmed that the objective gene of the cell wall lytic enzyme was present in the DNA fragment of 2.8 kbp.

By sub-cloning the fragment containing the gene of the cell wall lytic enzyme, a plasmid was prepared. The plasmid was used for transformation into *E. coli*, to recover a transformant.

The present invention will now be described in detail hereinbelow.

As has been described above, the gene of a cell wall lytic enzyme enzyme of the present invention is derived from microorganism having an ability of producing a cell wall lytic enzume.

The microorganism having an ability of producing the cell wall lytic enzyme include for example Actinomycetes of genus Streptomyces, and bacteria belonging to genera Achromobacter, Aeromonas, Bacillus, Clostridium, Flavobacterium, Myxobacter, Myxococcus, Pseudomonas, Staphylococcus, Streptococcus and the like.

Among them, preferably, use is made of bacteria belonging to genus Streptomyces. The bacterial strains belonging to genus Streptomyces include for example *Streptomyces rutgersensis* H-46 etc.

The cell wall lytic enzyme can be recovered from the aforementioned microorganisms. More specifically, the aforementioned bacterial strains are cultured by routine methods. The culture medium is preferably a medium containing defatted soy bean extract, but is not limited to. Cultivation can be carried out for example by the method by Hayashi K., et al., J. Ferment. Technol. (European Edition of Japanese Journal of Fermentation Engineering Association), Vol. 59, pp. 319–323, 1981.

The culture broth is centrifuged to remove the microorganism. From the supernatant thus obtained, a highly purified cell wall lytic enzyme can be recovered by routine purification means, such as ion exchange chromatography, column chromatography, FPLC, HPLC, etc.

One example of such purification means includes the method by Hayashi K., et al., Agric. Biol. Chem. (European Edition of Japanese Journal of Agriculture, Biochemistry and Chemistry), Vol. 45, pp. 2289–2300, 1981. More specifically, the enzyme can be purified by utilizing column chromatography on a cation exchange resin.

Then, the amino acid sequence at the N-terminus of the purified cell wall lytic enzyme was determined. For sequencing, a protein sequencer of Type G 1005A (manufactured by Hewlett Packard, Co.) can be used. The determined amino acid sequence at the N-terminus is shown as Sequence No. 3 in the Sequence Listing.

By determining the nucleotide sequence from the determined amino acid sequence and preparing primers (see Sequence Nos. 4 and 5 in the Sequence Listing) prepared on the basis of the nucleotide sequence, PCR was carried out with the genomic DNA extracted from the bacterial strain belonging to genus Streptomyces as a template by using said primers. Consequently, a prominent band of 140 bp was recovered.

So as to analyze the DNA nucleotide sequence of the resulting band, the band was cloned for the analysis with a DNA sequencer. The nucleotide sequence thus recovered by the analysis (see Sequence No. 6 in the Sequence Listing) was then translated into amino acid. Consequently, it was observed a sequence corresponding to the preliminarily amino acid sequence at the N-terminus (see Sequence No. 3 in the Sequence Listing), which indicates that the product recovered by PCR was a part of the gene of the cell wall lytic enzyme.

Then, the gene of the precursor, including the gene of the mature cell wall lytic enzyme, was cloned, by using the PCR product as a probe.

Firstly, genomic DNA is extracted from a bacterium belonging to genus Streptomyces. The extraction can be carried out for example by the method by Saito, "Protein and Nucleic Acid and Enzyme", Vol.11, pp.446. More specifically, the cell wall of the bacterium was enzymatically degraded, to wind the extracted DNA over a glass bar, to purify the genomic DNA.

The nucleotide sequence and amino acid sequence of the precursor of the cell wall lytic enzyme in accordance with the present invention are shown in Sequence No. 1 in the Sequence Listing. From the amino acid sequence of the precursor gene of said gene of the cell wall lytic enzyme, furthermore, the amino acid sequence of the gene of the cell wall lytic enzyme was constructed on the basis of the preliminarily determined amino acid sequence at the N-terminus of the cell wall lytic enzyme (see Sequence No. 3 in the Sequence Listing). The amino acid sequence of said gene is shown together with the nucleotide sequence thereof in Sequence No. 2 in the Sequence Listing.

The gene of the cell wall lytic enzyme in accordance with the present invention is an enzyme with a novel amino acid sequence, and no protein with 55% or higher homology to the enzyme has been found.

By subcloning the 2.8-kbp fragment prepared by agarose gel electrophoresis by using a DNA ligation kit (manufactured by Takara Brewery, Co.) in a plasmid preliminarily dephosphorylated, a plasmid pUC 18-SR1 was prepared.

The plasmid was then transformed into *E. coli* by routine method. The transformed *E. coli* has been deposited as the accession No. FERM BP-6166 at National Institute of Bioscience and Human Technology, Agency of Industrial Science and Technology (1–3, Higashi 1-chome, Tsukuba-shi, Ibaraki-ken, Japan). Furthermore, the plasmid pUC 18-SR1 contains the gene of the cell wall lytic enzyme.

The expression of the gene of the cell wall lytic enzyme can be confirmed, by culturing the transformant *E. coli* thus recovered and assaying said *E. coli* and the cell wall lytic enzyme in the supernatant.

By culturing the transformant in a nutrition medium at 20 to 37° C. for 3 to 48 hours and disrupting the resulting microbial strain and purifying the supernatant recovered by separation of the liquid from the solid in accordance with a routine method, the cell wall lytic enzyme can be recovered.

According to the present invention, the gene of the enzyme acting with bacterial cell wall to decompose the cell wall is provided. The enzyme recovered through the expression of the gene is useful in the field of food industry.

EXAMPLES

The present invention will now be illustrated in detail by referring to the following example.

Example 1

Microorganism *Streptomyces rutgersensis* H-46 was cultured in a culture medium containing 0.5% glucose and 2% defatted soy bean hot-water extract by the method by Hayashi K., et al., J. Ferment. Technol. (European Edition of Japanese Journal of Fermentation Engineering Association), Vol. 59, pp. 319–323, 1981.

From the supernatant recovered by eliminating the microbial strain from the culture broth, a highly purified cell wall lytic enzyme was recovered, by utilizing ion exchange chromatography by the method by Hayashi K., et al., Agric. Biol. Chem. (European Edition of Japanese Journal of Agriculture, Biochemistry and Chemistry), Vol. 45, pp. 2289–2300, 1981.

Using the purified enzyme, the amino acid sequence at the N-terminus was determined by a protein sequencer Type G 1005A (manufactured by Hewlett Packard, Co.). The determined sequence is shown as Sequence No. 3 in the Sequence Listing.

From the amino acid sequence determined, two regions with less codon stringency were selected, to chemically synthesize a forward primer (as described as Sequence No. 4 in the Sequence Listing) and a reverse primer (as described as Sequence No. 5 in the Sequence Listing).

Using these primers, amplification was effected by PCR, with the genomic DNA of the strain H-46 of *Streptomyces rutgersensis* as a template. Consequently, a prominent band of 140 bp was recovered.

By cloning the resulting band and analyzing the band with a DNA sequencer, determined was the DNA nucleotide sequence thereof as described in Sequence No. 6 in the Sequence Listing. The DNA nucleotide sequence was then translated into amino acid. It was observed a sequence corresponding to the preliminarily recovered amino acid sequence at the N-terminus as shown as Sequence No. 3 in the Sequence Listing.

It is thus indicated that the PCR product was a part of the gene of the cell wall lytic enzyme.

Then, the PCR product was labeled with Gene Image Chemiluminescence Nucleic Acid Detection System (manufactured by Amersham, Co.), and by using the labeled product as the probe, the gene of the precursor of the cell wall lytic enzyme was cloned.

Alternatively, the genomic DNA was extracted from *Streptomyces rutgersensis* H-46 by the method of Saito; "Protein, Nucleic Acid and Enzyme", Vol. 11, pp. 446. The genomic DNA was then completely decomposed with a restriction enzyme Sac I. The resulting restriction cleavage products were separated by agarose gel electrophoresis, and then subjected to Southern hybridization ("Cloning and Sequence", Watanabe eds. Noson Bunka-sha, 1989, pp. 157). Consequently, it was confirmed that the objective gene of the cell wall lytic enzyme was present in the DNA fragment of 2.8 kbp.

The 2.8 kbp fragment was prepared by agarose gel electrophoresis, according to the method described in Sambrook, J., Fritsch, E. F. and Maniatis, T., "Molecular Cloning; A Laboratory Manual, 2nd edition", Section 6.3, Vol. 1 (1989).

Alternatively, the plasmid pUS-18 was cleaved with a restriction enzyme Sac I, followed by dephosphorylation with alkali phosphatase. The 2.8 kbp fragment was subcloned into the dephosphorylated plasmid by using a DNA ligation kit (manufactured by Takara Brewery, Co.) by the method described in Cloning and Sequence, Watanabe eds. Noson Bunka-sha, 1989, pp. 134, to prepare a plasmid pUC 18-SR1.

The plasmid was transformed into *E. coli*, according to the method described in Sambrook, J., Fritsch, E. F. and Maniatis, T., "Molecular Cloning; A Laboratory Manual, 2nd edition", Section 1.74, Vol. 1 (1989).

The transformed *E. coli* has been deposited at National Institute of Bioscience and Human Technology, Agency of Industrial Science and Technology, ant the accession No. thereof is FERM BP-6166. Furthermore, the plasmid PUC 18-SR1 contains the gene of the cell wall lytic enzyme. The transformant according to claim 6 can also be obtained by the same method.

A greater volume of the plasmid pUS 18-SR1 was prepared from the transformant, for analysis with d-Rhodamine-Terminator Cycle Sequencing Kit (manufactured by Perkin Elmer, Co.).

Linking the information of the determined nucleotide sequence together, the gene of the precursor of the cell wall lytic enzyme was constructed. The nucleotide sequence and amino acid sequence of said gene of the precursor are shown as Sequence No.1 in the Sequence Listing.

The amino acid sequence of the precursor gene of the cell wall lytic enzyme, as shown as Sequence No. 1 in the Sequence Listing, is compared with the preliminarily recovered amino acid sequence of the N-terminus of the cell wall lytic enzyme (see Sequence No. 3 in the Sequence Listing).

Consequently, the amino acid sequence of the N-terminus of the cell wall lytic enzyme (see Sequence No. 3 in the Sequence Listing) agrees with the sequence from the 21st residue to 100th residue in the amino acid sequence as shown in Sequence No. 1. It is thus indicated that the gene of the cell wall lytic enzyme can be found downstream the 241st residue of the nucleotide sequence of the precursor gene. The gene of the active cell wall lytic enzyme was constructed from the precursor gene of the cell wall lytic enzyme, on the basis of the amino acid sequence of the N-terminus of the cell wall lytic enzyme, which is shown in Sequence No. 2 in the Sequence Listing.

The molecular weight of the active cell wall lytic enzyme was determined by a laser ionization system Type TOF-MS KOMPACT MALDI III manufactured by Shimadzu. Co. Ltd. The molecular weight was 23,000 daltons, which agrees well with the molecular weight of the protein encoded by the present gene, i.e. 23,056 daltons.

The entire disclosure of Japanese Patent Application No. 9-343630 filed on Dec. 1, 1997 including specification, claims and summary are incorporated herein by reference in its entirety.

What is claimed is:

1. An isolated and purified polynucleotide encoding the polypeptide of SEQ ID NO: 7 or 8.

2. The isolated and purified polynucleotide of claim 1, which encodes the polypeptide of SEQ ID NO: 7.

3. The isolated and purified polynucleotide of claim 1, which encodes the polypeptide of SEQ ID NO: 8.

4. An isolated and purified polynucleotide comprising SEQ ID NO: 1 or 2.

5. The isolated and purified polynucleotide of claim 4, which comprises SEQ ID NO: 1.

6. The isolated and purified polynucleotide of claim 4, which comprises SEQ ID NO: 2.

7. A vector comprising the polynucleotide of claim 1.

8. A vector comprising the polynucleotide of claim 2.

9. A vector comprising the polynucleotide of claim 3.

10. A vector comprising the polynucleotide of claim 4.

11. A vector comprising the polynucleotide of claim 5.

12. A vector comprising the polynucleotide of claim 6.

13. An *E. coli* host cell transformed with the vector of claim 7.

14. An *E. coli* host cell transformed with the vector of claim 8.

15. An *E. coli* host cell transformed with the vector of claim 9.

16. An *E. coli* host cell transformed with the vector of claim 10.

17. An *E. coli* host cell transformed with the vector of claim 11.

18. An *E. coli* host cell transformed with the vector of claim 12.

19. A transformed *E. coli* deposited under the Accession No. FERM BP-6166.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 1088 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Steptomyces rutgersensis (B) STRAIN: H-46
           (C) INDIVIDUAL ISOLATE: Name of Plasmid: pUC 18-SR1

(ix) FEATURE:
           (A) NAME/KEY: CDS
           (B) LOCATION: 181..870
           (D) OTHER INFORMATION: /note= "METHOD OF DETERMINING THE
               CHARACTERISTICS: P"

(xi) SEQUENCE DESCRIPTION: SEQ ID NO:1:

```
TCAGGCACCC CCCGTCACGC TCGCCCACCG CCTTCGGAGG CCCCCATGCG CGTACCCAGA      60

TCCGGAGCCC GCCCCTCTCG CCGCACCGCG GCCGGAGTTC TCCTCGCCGC CCTCTCCCTG     120

CTCTTCACCC TGCCCTCGGG GGCGCACGCC GCCGACCGTC CCGAGCGGGG CGAGGCCCAC     180

ATG GGC ATG GGC GTC GTG GAG CAC GAC GGC CGG AGC GGG GCG CCC GGT      228
Met Gly Met Gly Val Val Glu His Asp Gly Arg Ser Gly Ala Pro Gly
  1               5                  10                  15

ATC TCG CCG CGC GCC GTG CAG ACG GAG GGC GTG GAC GTC TCC AGC CAT      276
Ile Ser Pro Arg Ala Val Gln Thr Glu Gly Val Asp Val Ser Ser His
             20                  25                  30

CAG GGG AAC GTC GAC TGG GCC GCG CTG TGG AAC AGC GGC GTC AAG TGG      324
Gln Gly Asn Val Asp Trp Ala Ala Leu Trp Asn Ser Gly Val Lys Trp
         35                  40                  45

TCG TAC GTG AAG GCC ACC GAG GGC ACG TAC TAC AAG AAC CCG TAC TTC      372
Ser Tyr Val Lys Ala Thr Glu Gly Thr Tyr Tyr Lys Asn Pro Tyr Phe
 50                  55                  60

GCG CAG CAG TAC AAC GGC AGT TAC AAC GTG GGG ATG ATC CGC GGC GCC      420
Ala Gln Gln Tyr Asn Gly Ser Tyr Asn Val Gly Met Ile Arg Gly Ala
 65                  70                  75                  80

TAC CAC TTC GCG ACG CCC AAC ACG ACG AGC GGC GCC GCC CAG GCC AAC      468
Tyr His Phe Ala Thr Pro Asn Thr Thr Ser Gly Ala Ala Gln Ala Asn
                 85                  90                  95

TAC TTC GTG GAC AAC GGC GGC GGC TGG TCC CGC GAC GGC AAG ACC CTG      516
Tyr Phe Val Asp Asn Gly Gly Gly Trp Ser Arg Asp Gly Lys Thr Leu
            100                 105                 110

CCG GGT GTC CTG GAC ATC GAG TGG AAC CCG TAC GGC GAC CAG TGC TAC      564
Pro Gly Val Leu Asp Ile Glu Trp Asn Pro Tyr Gly Asp Gln Cys Tyr
        115                 120                 125

GGC CTG AGC CAG TCC GCG ATG GTC AAC TGG ATC CGC GAC TTC ACC AAC      612
Gly Leu Ser Gln Ser Ala Met Val Asn Trp Ile Arg Asp Phe Thr Asn
    130                 135                 140

ACC TAC AAG GCC CGC ACC GGC CGG GAC GCG GTC ATC TAC ACC GCG ACC      660
Thr Tyr Lys Ala Arg Thr Gly Arg Asp Ala Val Ile Tyr Thr Ala Thr
145                 150                 155                 160

AGC TGG TGG ACC TCC TGC ACC GGC AAC TAC GCG GGC TTC GGC ACC ACC      708
Ser Trp Trp Thr Ser Cys Thr Gly Asn Tyr Ala Gly Phe Gly Thr Thr
                165                 170                 175

AAC CCG CTC TGG GTC GCC CGG TAC GCC GCC TCG GTG GGC GAA CTC CCG      756
Asn Pro Leu Trp Val Ala Arg Tyr Ala Ala Ser Val Gly Glu Leu Pro
            180                 185                 190

GCC GGC TGG GGC TTC TAC ACG ATG TGG CAG TAC ACC TCC ACC GGC CCG      804
Ala Gly Trp Gly Phe Tyr Thr Met Trp Gln Tyr Thr Ser Thr Gly Pro
        195                 200                 205

ATC GTC GGC GAC CAC AAC CGC TTC AAC GGC GCG TAC GAC CGG CTC CAG      852
Ile Val Gly Asp His Asn Arg Phe Asn Gly Ala Tyr Asp Arg Leu Gln
    210                 215                 220

GCG CTC GCC AAC GGC TGA GCCCGAGCCG TCGGACGCCC CGGCGACCGC             900
Ala Leu Ala Asn Gly *
225                 230

GCACGCCGAA GAGGCCCGGT GACCTGTTCA CCGGGCCTTT TCCGGGTCCG GAGCGGGGTG     960

CGGAAATCCT TCCGGGGGCG GGGCAACCGT TCGACTATCC ACTCCATCTA TACACGGCGT    1020
```

```
GAACACTCTG ACGCACGCCG AGCCCCGCAC CCGCCGCCGC CCGCACCGCA TCCGCCGTAC    1080

AGCCGTCG                                                              1088

(2) INFORMATION FOR SEQ ID NO:2:

(i) SEQUENCE CHARACTERISTICS:
        (A) LENGTH: 630 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Steptomyces rutgersensis
        (B) STRAIN: H-46
        (C) INDIVIDUAL ISOLATE: Name of Plasmid: pUC 18-SR1

(ix) FEATURE:
        (A) NAME/KEY: mat_peptide
        (B) LOCATION: 1..630
        (D) OTHER INFORMATION: /note= "METHOD OF DETERMINING THE
            CHARACTERISTICS: P"

(xi) SEQUENCE DESCRIPTION: SEQ ID NO:2:

GCC GTG CAG ACG GAG GGC GTG GAC GTC TCC AGC CAT CAG GGG AAC GTC         48
Ala Val Gln Thr Glu Gly Val Asp Val Ser Ser His Gln Gly Asn Val
  1               5                  10                  15

GAC TGG GCC GCG CTG TGG AAC AGC GGC GTC AAG TGG TCG TAC GTG AAG         96
Asp Trp Ala Ala Leu Trp Asn Ser Gly Val Lys Trp Ser Tyr Val Lys
             20                  25                  30

GCC ACC GAG GGC ACG TAC TAC AAG AAC CCG TAC TTC GCG CAG CAG TAC        144
Ala Thr Glu Gly Thr Tyr Tyr Lys Asn Pro Tyr Phe Ala Gln Gln Tyr
         35                  40                  45

AAC GGC AGT TAC AAC GTG GGG ATG ATC CGC GGC GCC TAC CAC TTC GCG        192
Asn Gly Ser Tyr Asn Val Gly Met Ile Arg Gly Ala Tyr His Phe Ala
     50                  55                  60

ACG CCC AAC ACG ACG AGC GGC GCC GCC CAG GCC AAC TAC TTC GTG GAC        240
Thr Pro Asn Thr Thr Ser Gly Ala Ala Gln Ala Asn Tyr Phe Val Asp
 65                  70                  75                  80

AAC GGC GGC GGC TGG TCC CGC GAC GGC AAG ACC CTG CCG GGT GTC CTG        288
Asn Gly Gly Gly Trp Ser Arg Asp Gly Lys Thr Leu Pro Gly Val Leu
                 85                  90                  95

GAC ATC GAG TGG AAC CCG TAC GGC GAC CAG TGC TAC GGC CTG AGC CAG        336
Asp Ile Glu Trp Asn Pro Tyr Gly Asp Gln Cys Tyr Gly Leu Ser Gln
            100                 105                 110

TCC GCG ATG GTC AAC TGG ATC CGC GAC TTC ACC AAC ACC TAC AAG GCC        384
Ser Ala Met Val Asn Trp Ile Arg Asp Phe Thr Asn Thr Tyr Lys Ala
        115                 120                 125

CGC ACC GGC CGG GAC GCG GTC ATC TAC ACC GCG ACC AGC TGG TGG ACC        432
Arg Thr Gly Arg Asp Ala Val Ile Tyr Thr Ala Thr Ser Trp Trp Thr
    130                 135                 140

TCC TGC ACC GGC AAC TAC GCG GGC TTC GGC ACC ACC AAC CCG CTC TGG        480
Ser Cys Thr Gly Asn Tyr Ala Gly Phe Gly Thr Thr Asn Pro Leu Trp
145                 150                 155                 160

GTC GCC CGG TAC GCC GCC TCG GTG GGC GAA CTC CCG GCC GGC TGG GGC        528
Val Ala Arg Tyr Ala Ala Ser Val Gly Glu Leu Pro Ala Gly Trp Gly
                165                 170                 175

TTC TAC ACG ATG TGG CAG TAC ACC TCC ACC GGC CCG ATC GTC GGC GAC        576
Phe Tyr Thr Met Trp Gln Tyr Thr Ser Thr Gly Pro Ile Val Gly Asp
            180                 185                 190

CAC AAC CGC TTC AAC GGC GCG TAC GAC CGG CTC CAG GCG CTC GCC AAC        624
His Asn Arg Phe Asn Gly Ala Tyr Asp Arg Leu Gln Ala Leu Ala Asn
        195                 200                 205
```

```
GGC TGA                                                              630
Gly *
    210
```

(2) INFORMATION FOR SEQ ID NO:3:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (vi) ORIGINAL SOURCE:
        (A) ORGANISM: Streptomyces rutgersensis
        (B) STRAIN: H-46
        (C) INDIVIDUAL ISOLATE: Enzyme produced by Streptomyces
            rutgersensis (xi) SEQUENCE DESCRIPTION: SEQ ID NO:3:

```
Ala Val Gln Thr Glu Gly Val Asp Val Ser Ser His Gln Gly Asn Val
1               5                   10                  15

Asp Trp Ala Ala Leu Trp Asn Ser Gly Val Lys Trp Ser Tyr Val Lys
            20                  25                  30

Ala Thr Glu Gly Thr Tyr Tyr Lys Asn Pro Tyr Phe Ala Gln Gln Tyr
                35                  40                  45

Asn Gly Ser Tyr Asn Val Gly Met Ile Arg Gly Ala Tyr His Phe Ala
        50                  55                  60

Thr Pro Asn Thr Thr Ser Gly Ala Ala Gln Ala Asn Tyr Phe Val Asp
65                  70                  75                  80
```

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "(prepared from amino acid
            sequence)"

(vi) ORIGINAL SOURCE:
        (A) ORGANISM: Steptomyces rutgersensis
        (B) STRAIN: H-46
        (C) INDIVIDUAL ISOLATE: Enzyme produced by Streptomyces
            rutgersensis (xi) SEQUENCE DESCRIPTION: SEQ ID NO:4:

```
CARGGSAAYG TSGAYTGGGC                                                 20
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "(prepared from amino acid
            sequence)"

(vi) ORIGINAL SOURCE:
        (A) ORGANISM: Streptomyces rutgersensis
        (B) STRAIN: H-46

(C) INDIVIDUAL ISOLATE: Enzyme produced by Streptomyces
                rutgersensis (xi) SEQUENCE DESCRIPTION: SEQ ID NO:5:

CGGATCATSC CSACRTTRTA                                                    20

(2) INFORMATION FOR SEQ ID NO:6:

(i) SEQUENCE CHARACTERISTICS:
        (A) LENGTH: 137 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR Products"

(vi) ORIGINAL SOURCE:
        (A) ORGANISM: Streptomyces rutgersensis
        (B) STRAIN: H-46
        (C) INDIVIDUAL ISOLATE: PCR product (xi) SEQUENCE DESCRIPTION: SEQ ID NO:6:

CAG GGG AAC GTC GAC TGG GCC GCG CTG TGG AAC AGC GGC GTC AAG TGG        48
Gln Gly Asn Val Asp Trp Ala Ala Leu Trp Asn Ser Gly Val Lys Trp
 1               5                  10                  15

TCG TAC GTG AAG GCC ACC GAG GGC ACG TAC TAC AAG AAC CCG TAC TTC        96
Ser Tyr Val Lys Ala Thr Glu Gly Thr Tyr Tyr Lys Asn Pro Tyr Phe
                20                  25                  30

GCG CAG CAG TAC AAC GGC AGT TAC AAC GTG GGG ATG ATC CG                137
Ala Gln Gln Tyr Asn Gly Ser Tyr Asn Val Gly Met Ile
            35                  40              45

(2) INFORMATION FOR SEQ ID NO:7:

(i) SEQUENCE CHARACTERISTICS:
        (A) LENGTH: 229 amino acids
        (B) TYPE: amino acid
        (D) TOPOLOGY: linear (ii) MOLECULE TYPE: protein (xi) SEQUENCE DESCRIPTION: SEQ ID NO:7:

Met Gly Met Gly Val Val Glu His Asp Gly Arg Ser Gly Ala Pro Gly
 1               5                  10                  15

Ile Ser Pro Arg Ala Val Gln Thr Glu Gly Val Asp Val Ser Ser His
                20                  25                  30

Gln Gly Asn Val Asp Trp Ala Ala Leu Trp Asn Ser Gly Val Lys Trp
            35                  40                  45

Ser Tyr Val Lys Ala Thr Glu Gly Thr Tyr Tyr Lys Asn Pro Tyr Phe
        50                  55                  60

Ala Gln Gln Tyr Asn Gly Ser Tyr Asn Val Gly Met Ile Arg Gly Ala
65                  70                  75                  80

Tyr His Phe Ala Thr Pro Asn Thr Thr Ser Gly Ala Ala Gln Ala Asn
                85                  90                  95

Tyr Phe Val Asp Asn Gly Gly Trp Ser Arg Asp Gly Lys Thr Leu
                100                 105                 110

Pro Gly Val Leu Asp Ile Glu Trp Asn Pro Tyr Gly Asp Gln Cys Tyr
            115                 120                 125

Gly Leu Ser Gln Ser Ala Met Val Asn Trp Ile Arg Asp Phe Thr Asn
130                 135                 140

Thr Tyr Lys Ala Arg Thr Gly Arg Asp Ala Val Ile Tyr Thr Ala Thr
145                 150                 155                 160

```
Ser Trp Trp Thr Ser Cys Thr Gly Asn Tyr Ala Gly Phe Gly Thr Thr
            165                 170                 175

Asn Pro Leu Trp Val Ala Arg Tyr Ala Ala Ser Val Gly Glu Leu Pro
            180                 185                 190

Ala Gly Trp Gly Phe Tyr Thr Met Trp Gln Tyr Thr Ser Thr Gly Pro
            195                 200                 205

Ile Val Gly Asp His Asn Arg Phe Asn Gly Ala Tyr Asp Arg Leu Gln
210                 215                 220

Ala Leu Ala Asn Gly
225
```

(2) INFORMATION FOR SEQ ID NO:8:

(i) SEQUENCE CHARACTERISTICS:
        (A) LENGTH: 209 amino acids
        (B) TYPE: amino acid
        (D) TOPOLOGY: linear (ii) MOLECULE TYPE: protein (xi) SEQUENCE DESCRIPTION: SEQ ID NO:8:

```
Ala Val Gln Thr Glu Gly Val Asp Val Ser Ser His Gln Gly Asn Val
1               5                   10                  15

Asp Trp Ala Ala Leu Trp Asn Ser Gly Val Lys Trp Ser Tyr Val Lys
            20                  25                  30

Ala Thr Glu Gly Thr Tyr Tyr Lys Asn Pro Tyr Phe Ala Gln Gln Tyr
            35                  40                  45

Asn Gly Ser Tyr Asn Val Gly Met Ile Arg Gly Ala Tyr His Phe Ala
        50                  55                  60

Thr Pro Asn Thr Thr Ser Gly Ala Ala Gln Ala Asn Tyr Phe Val Asp
65                  70                  75                  80

Asn Gly Gly Gly Trp Ser Arg Asp Gly Lys Thr Leu Pro Gly Val Leu
            85                  90                  95

Asp Ile Glu Trp Asn Pro Tyr Gly Asp Gln Cys Tyr Gly Leu Ser Gln
            100                 105                 110

Ser Ala Met Val Asn Trp Ile Arg Asp Phe Thr Asn Thr Tyr Lys Ala
            115                 120                 125

Arg Thr Gly Arg Asp Ala Val Ile Tyr Thr Ala Thr Ser Trp Trp Thr
130                 135                 140

Ser Cys Thr Gly Asn Tyr Ala Gly Phe Gly Thr Thr Asn Pro Leu Trp
145                 150                 155                 160

Val Ala Arg Tyr Ala Ala Ser Val Gly Glu Leu Pro Ala Gly Trp Gly
            165                 170                 175

Phe Tyr Thr Met Trp Gln Tyr Thr Ser Thr Gly Pro Ile Val Gly Asp
            180                 185                 190

His Asn Arg Phe Asn Gly Ala Tyr Asp Arg Leu Gln Ala Leu Ala Asn
            195                 200                 205

Gly
```

(2) INFORMATION FOR SEQ ID NO:9:

(i) SEQUENCE CHARACTERISTICS:
        (A) LENGTH: 45 amino acids
        (B) TYPE: amino acid
        (D) TOPOLOGY: linear (ii) MOLECULE TYPE: protein (xi) SEQUENCE DESCRIPTION: SEQ ID NO:9:

-continued

```
Gln Gly Asn Val Asp Trp Ala Ala Leu Trp Asn Ser Gly Val Lys Trp
 1               5                  10                  15

Ser Tyr Val Lys Ala Thr Glu Gly Thr Tyr Tyr Lys Asn Pro Tyr Phe
            20                  25                  30

Ala Gln Gln Tyr Asn Gly Ser Tyr Asn Val Gly Met Ile
            35                  40                  45
```